United States Patent [19]

Sakano et al.

[11] Patent Number: 4,524,147
[45] Date of Patent: Jun. 18, 1985

[54] URACIL DERIVATIVES, PROCESS FOR PREPARING SAME, AND PHARMACEUTICAL COMPOSITIONS COMPRISING SAME

[75] Inventors: Isao Sakano; Tatsuro Yokoyama; Seitaro Kajiya, all of Yokohama; Yutaka Okazaki, Mobara; Hiroshi Tokuda, Mobara; Hiroshi Kawazura, Mobara; Mikio Kumakura, Mobara; Akira Awaya, Yokohama, all of Japan

[73] Assignee: Mitsui Toatsu Chemicals, Incorporated, Tokyo, Japan

[21] Appl. No.: 444,571

[22] PCT Filed: Mar. 24, 1982

[86] PCT No.: PCT/JP82/00081
§ 371 Date: Nov. 16, 1982
§ 102(e) Date: Nov. 16, 1982

[87] PCT Pub. No.: WO82/03392
PCT Pub. Date: Oct. 14, 1982

[30] Foreign Application Priority Data

Mar. 24, 1981 [JP] Japan .................. 56-41752

[51] Int. Cl.³ .................. A61K 31/505; C07D 403/02
[52] U.S. Cl. .................. 514/274; 544/229; 544/296
[58] Field of Search .................. 544/296; 424/251

[56] References Cited

U.S. PATENT DOCUMENTS 3,532,699 10/1970 Kugele .................. 544/296

FOREIGN PATENT DOCUMENTS

WO82/03392 10/1982 PCT Int'l Appl. .

OTHER PUBLICATIONS

Kugele, "Chemical Abstracts", vol. 71, 1961, col. 70628a.
"Chemical Abstracts", vol. 98, 1983, col. 98:126145t.

Primary Examiner—Glennon H. Hollrah
Assistant Examiner—James H. Turnipseed
Attorney, Agent, or Firm—Fisher, Christen & Sabol

[57] ABSTRACT

Disclosed are uracil derivatives having the general formula

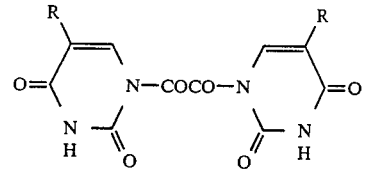

where R represents a hydrogen atom or an alkyl radical having 1 to 4 carbon atoms. Also disclosed are a process for preparing these compounds and pharmaceutical compositions having immunomodulatory activity which comprise these compounds as the active ingredient.

9 Claims, No Drawings

URACIL DERIVATIVES, PROCESS FOR PREPARING SAME, AND PHARMACEUTICAL COMPOSITIONS COMPRISING SAME

DESCRIPTION

1. Cross-Reference to Related Applications

This application is a national stage application of international application No. PCT/JP82/00081 filed Mar. 24, 1982.

2. Technical Field

This invention relates to novel uracil derivatives, a process for preparing the same, and pharmaceutical compositions comprising the same. More particularly, it relates to novel uracil derivatives which have such immunomodulatory activity as to make them effective against immune diseases (e.g., rheumatoid arthritis) and also useful in the treatment of viral diseases and in the immunotherapy of cancer and, moreover, are very desirable for therapeutic purposes because of their low toxicity, a process for preparing the same, and pharmaceutical compositions comprising the same.

3. Background Art

Conventionally, a large number of steroidal and non-steroidal anti-inflammatory agents have been used in the clinical treatment of autoimmune diseases such as rheumatism and the like. However, these numerous drugs are still not entirely satisfactory, judging from their pharmacological actions, side effects, toxicity, and the like.

DISCLOSURE OF THE INVENTION

It is an object of the present invention to provide a novel uracil derivative which exerts a specific effect on the cells participating in immune responses and thereby serves to modify the immune responses of the host, and a process for preparing this compound.

It is another object of the present invention to provide a pharmaceutical composition characterized by immunomodulatory activity and low toxicity.

In accordance with one feature of the present invention, there is provided a uracil derivative having the general formula

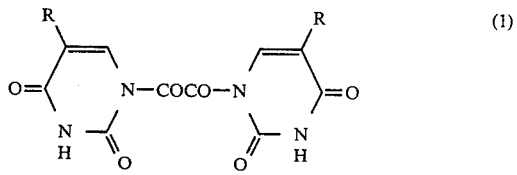

where R represents a hydrogen atom or an alkyl radical having 1 to 4 carbon atoms.

In accordance with another feature of the present invention, compounds of the general formula (1) can be prepared by reacting a silylated pyrimidine of the general formula

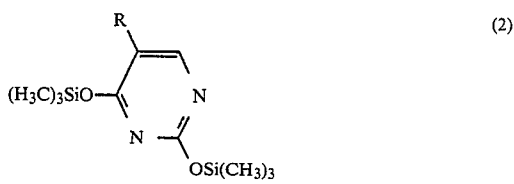

where R represents a hydrogen atom or an alkyl radical having 1 to 4 carbon atoms, with a compound of the general formula $$X\text{-COCO-}X \tag{3}$$

where X represents a halogen atom or an alkoxy radical having 1 to 4 carbon atoms.

In accordance with still another feature of the present invention, a pharmaceutical composition having immunomodulatory activity comprises a compound of the general formula (1) and a pharmaceutically acceptable carrier.

BEST MODE FOR CARRYING OUT THE INVENTION

Specific examples of the uracil derivatives represented by the general formula (1) include bis[2,4-dioxo-(1H,3H)pyrimidin-1-yl]ethanedione, bis[2-4-dioxo-5-methyl-(1H,3H)pyrimidin-1-yl]ethanedione, bis[2,4-dioxo-5-ethyl-(1H,3H)pyrimidin-1-yl]ethanedione, bis[2,4-dioxo-5-n-propyl-(1H,3H)pyrimidin-1-yl]ethanedione, bis[2,4-dioxo-5-isopropyl-(1H,3H)pyrimidin-1-yl]ethanedione, bis[2,4-dioxo-5-n-butyl(1H,3H)pyrimidin-1-yl]ethanedione, and bis[2,4-dioxo-5-tert-butyl-(1H,3H)pyrimidin-1yl]ethanedione. It is to be understood that the pyrimidine rings present in the general formula (1) can take various tautomeric forms.

In preparing such uracil derivatives according to the process of the present invention, not less than 2 moles, preferably 2 moles, of a silylated pyrimidine of the general formula (2) is reacted with 1 mole of a compound of the general formula (3) in the presence of a solvent. Generally, uracils are hardly soluble in solvents and hence fail to give a satisfactorily high reaction rate. For this reason, they are modified by silylation and used as active compounds soluble in solvents. Although such compounds can be isolated and purified by distillation or other suitable techniques, silylated pyrimidines of the general formula (2) may be used without purification.

Specific examples of the silylating agents suitable for this purpose include trimethylchlorosilane, hexamethyldisilazane, N,O-bis(trimethylsilyl)acetamide, N,O-bis(-trimethylsilyl)-trifluoroacetamide, and the like. Where hexamethyldisilazane is used, it is usually advantageous to use it in combination with trimethylchlorosilane. The silylation of uracils with such a silylating agent can be carried out in the presence of a solvent such as pyridine or the like. Although these silylation reactions proceed at room temperature, they may be accelerated either with the aid of a catalyst such as ammonium sulfate or by the application of heat and/or pressure.

The reaction of a silylated pyrimidine of the general formula (2) with a compound of the general formula (3) is usually carried out in the presence of a solvent, and specific examples of the solvents suitable for this purpose include pyridine, tetrahydrofuran, dioxane, N,N-dimethylformamide, N,N-dimethylacetamide, acetonitrile, benzene, toluene, xylene, and the like. Where X in the general formula (3) is a halogen atom, it may be beneficial to use an acid acceptor such as triethylamine. Although this reaction proceeds at room temperature or below, the reaction system may be heated as desired. Specific examples of the comppounds represented by the general formula (3) include oxalyl chloride, oxalyl bromide, diethyl oxalate, di-tert-butyl oxalate, and the like.

The compounds of the present invention, which are within the scope of the above general formula (1), have pharmacological activities. Among others, it has unexpectedly been found that the compounds of the present invention have immunomodulatory activity. Moreover, the compounds of the present invention are very useful for therapeutic purposes because of their low toxicity.

These facts are more fully explained with reference to the following evaluation tests. A variety of experimental systems are being commonly used to test immunomodulatory activity in animals. Of such tests, the most typical one is an augmentation test of delayed hypersensitivity as shown below.

The delayed hypersensitivity induced in mice by applying picryl chloride (2-chloro-1,3,5-nitrobenzene) to the skin is known to be a typical phenomenon of cellular immunity and constitutes one of the experimental systems in world-wide use (Asherson, G. L., and Ptak, W. "Contact and delayed hypersensitivity in the mouse I. Active sensitization and passive transfer," Immunology, 15, 405–416(1968)).

In the following Evaluation Test 1, this experimental system was used to carry out an augmentation test of delayed hypersensitivity.

EVALUATION TEST 1

[Augmentation test of delayed hypersensitivity]

Test procedure:

Male mice of the ICR strain, weighing approximately 30 g, were used in groups of eight. These animals were sensitized by shaving the hair on the abdomen and applying thereto a 3% solution of picryl chloride in a 4:1 mixture of olive oil and acetone. Simultaneously with this sensitization, each of two compounds of the present invention was dissolved or suspended in physiological saline containing 0.2% carboxymethyl cellulose and administered orally to the animals in a dose of 50 mg per kg of body weight. A control group was treated solely with physiological saline containing 0.2% carboxymethyl cellulose.

Seven days after sensitization, delayed hypersensitivity was challenged by wrapping the tips of a forceps with pieces of felt, impregnating the felt with olive oil containing 1% picryl chloride, and pinching both ears of each animal. The thicknesses of the ears were measured before and 24 hours after the challenge, and the calculated percent increase of ear thickness (the average of 16 measurements made of the ears of 8 animals) is shown in Table 1. For purposes of comparison, the results of an experiment with Lavamisole hydrochloride are also given. The test results thus obtained were subjected to statistical analysis using the F.t test. The values marked with an asterisk (*) indicate that, when they were compared with the value of the control group, the differences were significant at P<0.05.

Results:

By administering the compounds of the present invention simultaneously with sensitization, the reaction evoked by a challenge was augmented. The activity of the compounds of the present invention was found to be equal to or higher than that of Levemisole used for comparative purposes. Thus, the compounds of the present invention are considered to have the ability to regulate cellular immune responses in mice (i.e., immunomodulatory activity).

TABLE 1

Test for Augmentation of Delayed Hypersensitivity

| Compound | Percent increase of ear thickness |
|---|---|
| (structure 1) | 33.9* |
| (structure 2) | 28.6 |
| Levamisole hydrochloride | 31.2* |

The adjuvant arthritis induced in rats by injection of a tubercle bacillus adjuvant is frequently used as an experimental model for rheumatoid arthritis in man.

Although the mechanism by which this phenomenon occurs is not completely elucidated, cellular immunity is known to play an important role. Employing this well-known adjuvant arthritis test, the same compounds of the present invention were further examined for immunomodulatory activity.

EVALUATION TEST 2

[Adjuvant arthritis test]

Test procedure:

An adjuvant was prepared by suspending 0.4 mg of killed and dried cells of the human type tubercle bacillus (Mycobacterium tuberclosis) in 0.1 ml of liquid paraffin, and inoculated intradermally into the right hind paw of 8-weeks-old male rats of the SD strain. Each of the two compounds of the present invention was subcutaneously administered nine times before and after injection of the adjuvant. These compounds were dissolved or suspended in physiological saline containing 0.2% carboxymethyl cellulose and administered in an amount of 5 mg per kg of body weight. The volume of the left hind paw of each animal was daily measured from the day of inoculation of the adjuvant to the end of the test, and the calculated percent inhibition of swelling is shown in Table 2. For purposes of comparison, the results of an experiment with Levamisole hydrochloride are also given. The test results thus obtained were subjected to statistical analysis using the F.t test. The values marked with an asterisk (*) indicate that, when they were compared with the value of a control group treated solely with physiological saline containing 0.2% carboxymethyl cellulose, the differences were significant at P<0.05.

Results:

The compounds of the present invention remarkably inhibited secondary inflammation of the adjuvant arthritis and their effect was statistically significant as compared with the control group. The activity of the compounds of the present invention was found to be higher than that of Levamisole used for comparative purposes. Thus, the compounds of the present invention are considered to have immunomodulatory activity and, in addition, an antiarthritic effect.

TABLE 2

Adjuvant Arthritis Test

| Compound | Number of animals | Percent inhibition of swelling as compared with control group (average of 16-20 days) |
|---|---|---|
| (structure: O=⟨pyrimidine-NH-C(=O)⟩—N—COCO—N—⟨pyrimidine-NH-C(=O)⟩=O) | 10 | 41.4* |
| (structure: dimethyl analog with H₃C and CH₃ substituents) | 10 | 29.9* |
| Levamisole hydrochloride | 44 | 19.8* |

As can be seen from Evaluation Tests 1 and 2, the compounds of the present invention have strong immunomodulatory activity. Accordingly, they are effective in the treatment of diseases which are known to involve impairments of or abnormalities in immunological function, for example, autoimmune diseases such as rheumatoid arthritis and the like.

The toxicity of the active ingredients of some typical pharmaceutical composition of the present invention was examined in the following Evaluation Test 3.

EVALUATION TEST 3

[Test for acute oral toxicity]

Test procedure:

Each of the compounds used in Evaluation Tests 1 and 2 was dissolved or suspended in physiological saline and administered orally to a group of 5 male mice of the ddY strain. The $LD_{50}$ value of the compound was estimated by observing these animals for 7 days after administration.

Results:

The $LD_{50}$ values of the above compounds were estimated to be not less than 1000 mg/kg. These values are far higher than the estimated $LD_{50}$ value (=200-300 mg/kg) of Levamisole hydrochloride, so that the active ingredients of the pharmaceutical compositions of the present invention are considered to have sufficiently low toxicity.

The pharmaceutical compositions of the present invention can be used in the same dosage forms and by the same administration methods as conventional immunomodulatory or anticancer agents. More specifically, for purposes of oral administration, they may be formed into capsules, granules, pills, subtle granules, tablets, syrups, and the like. For purposes of intrarectal administration, they are suitably formed into suppositories. For purposes of injection, they may be formed into subcutaneous, intramuscular, and intravenous injections.

The pharmaceutical compositions of the present invention preferably contain an active ingredient in an amount of approximately 10 to 95%, more preferably 15 to 90%, and are prepared according to per se well-known techniques such as blending, granulation, sugar coating, dissolution, and lyophilization. Where they are intended for oral use, the active ingredient is combined with a solid carrier and suitable pharmaceutic aids are added as desired. Specific examples of the useful carriers include sugars, cellulose preparations, calcium phosphate, and the like and specific examples of the useful pharmaceutic aids include binders, disintegrants (e.g., starch), flow controllers, lubricants, and the like. Moreover, any suitable additives may be incorporated according to the dosage form.

The indications for the pharmaceutical compositions of the present invention include a variety of diseases which are known to involve immunological disorder, and specific examples thereof are autoimmune diseases such as rheumatoid arthritis, multiple myositis, etc., various types of infection, various types of cancer, and the like. The pharmaceutical compositions of the present invention can be expected to normalize the immunological function of patients suffering from such diseases.

It is desirable that the administration method and dosage form of the pharmaceutical compositions of the present invention should suitable be determined according to the type of the disease, the condition of the patient, and the like. The daily dose per kilogram of body weight should usually be 0.5 to 100 mg, preferably 1 to 30 mg, for oral administration, 1 to 100 mg for intrarectal administration, 1 to 10 mg for intravenous administration, and 1 to 30 mg for subcutaneous or intramuscular administration. However, it is desirable to modify these doses properly according to the type of the disease, the condition of the patient, and the like. Depending on the type of the disease and the condition of the patient, the therapeutic effects of the active ingredient of the present invention can be enhanced by concomitantly using another drug or drugs as desired. By way of example, chemotherapeutic agents for cancer, such as alkylating agents, metabolic antagonists, and the like, cause the side effect of impairing the immunocompetence of the patient. When used in combination with such a drug, the active ingredient of the present invention can be expected to prevent manifestation of the above-described side effect of the drug and thereby enhance the therapeutic effects synergistically.

The process for preparing uracil derivatives according to the present invention is further illustrated by the following examples.

EXAMPLE 1

A homogeneous solution was prepared by adding 2.24 g of uracil to 20 ml of hexamethyldisilazane and stirring this mixture at 120° C. for approximately 30 minutes. The excess of hexamethyldisilazane was distilled off under reduced pressure, and the resulting residue was dissolved in 20 ml of dried tetrahydrofuran. This solution was cooled to 5° C. or below, and 1.27 g of oxalyl chloride was added thereto, followed by stirring for 30 minutes. Thereafter, 2.1 g of triethylamine was added thereto, followed by stirring for 30 minutes. Then, the reaction was continued at 50° C. for 2 hours. After the solvent and other volatile matter were removed from the reaction mixture under reduced pressure, the resulting residue was subjected to silical gel column chromatography, in which a yield of 1.37 g of bis[2,4-dioxo-(1H,3H)pyrimidin-1-yl]ethanedione was obtained by elution with a 20:1 mixture of chloroform and tetrahydrofuran.

Melting point: 260°–262° C. (decomposed)

| Elemental analysis: | | | |
|---|---|---|---|
| | C | H | N |
| Calculated value (%) for $C_{10}H_6N_4O_6$ | 43.18 | 2.17 | 20.14 |
| Found value (%) | 43.12 | 1.99 | 20.17 |

NMR spectrum ($\delta_{TMS}^{DMSO-d6}$,ppm): 6.10(2H, d, J=8.0 Hz), 8.20 (2H, d, J=8.0 Hz), 12.3 (2H, s, disappeared when the spectrum was recorded in $D_2O$).

EXAMPLE 2

Uracil was silylated by adding 3.4 g of uracil to 30 ml of N,O-bis(trimethylsilyl)acetamide and heating this mixture at 115° C. in a sealed tube. After the excess of N,O-bis(trimethylsilyl)acetamide, and the like were distilled off under reduced pressure, 2.2 g of diethyl oxalate and 50 ml of xylene were added to the residue. The resulting reaction mixture was heated at reflux temperature for 8 hours. The crude product separated from the reaction mixture by filtration was subjected to column chromatography, in which a yield of 1.71 g of bis[2,4-dioxo-(1H,3H)pyrimidin-1-yl]ethanedione was obtained under the same conditions as in Example 1.

EXAMPLE 3

A homogeneous solution was prepared by adding 2.52 g of thymine and 6 ml of hexamethyldisilazane to 20 ml of pyridine and stirring this mixture at reflux temperature for 4 hours. The excess of the silylating agent, pyridine, and the like were removed from the solution under reduced pressure, and the resulting residue was dissolved in 20 ml of tetrahydrofuran. This solution was kept at 5° C., and 1.27 g of oxalyl chloride and 2.0 g of triethylamine were added thereto. The resulting reaction mixture was stirred at room temperature for 1 hour and then at 40°–50° C. for 2 hours. After the solvent and other volatile matter were removed from the reaction mixture, the resulting crude product was subjected to column chromatography, in which a yield of 1.9 g of bis[5-methyl-2,4-dioxo-(1H,3H)pyrimidin-1-yl]ethanedione was obtained by elution with a 20:1 mixture of chloroform and tetrahydrofuran.

Melting point: 230°–232° C. (decomposed)

| Elemental analysis: | | | |
|---|---|---|---|
| | C | H | N |
| Calculated value (%) for $C_{12}H_{10}N_4O_6$ | 47.06 | 3.29 | 18.30 |
| Found value (%) | 47.11 | 3.30 | 18.41 |

NMR spectrum ($\delta_{TMS}^{DMSO-d6}$,ppm): 1.92 (6H, s), 8.06(2H, s), 12.16 (2H, s, disappeared when the spectrum was recorded in $D_2O$).

We claim:

1. A uracil derivative having the general formula

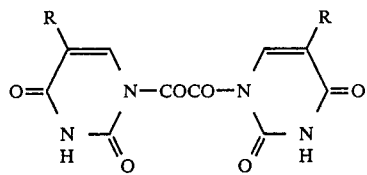

(1)

where R represents a hydrogen atom or an alkyl radical having 1 to 4 carbon atoms.

2. A uracil derivative as claimed in claim 1 wherein, in the general formula (1), R is a hydrogen atom or a methyl radical.

3. A uracil derivative as claimed in claim 2 which is bis[2,4-dioxo-(1H,3H)pyrimidin-1-yl]ethanedione.

4. A uracil derivative as claimed in claim 2 which is bis[5-methyl-2,4-dioxo-(1H,3H)pyrimidin-1-yl]ethanedione.

5. A process for preparing uracil derivatives of the general formula

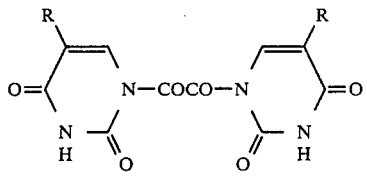

(1)

where R represents a hydrogen atom or an alkyl radical having 1 to 4 carbon atoms, which comprises reacting a silylated pyrimidine of the general formula

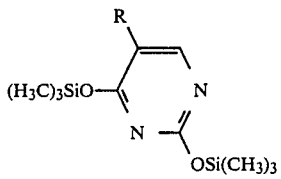

(2)

where R is as defined for the general formula (1), with a compound of the general formula

 X-COCO-X (3)

where X represents a halogen atom or an alkoxy radical having 1 to 4 carbon atoms.

6. A pharmaceutical composition having immunomodulatory activity which comprises an effective amount of a uracil derivative of the general formula

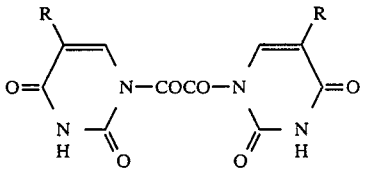

(1)

where R represents a hydrogen atom or an alkyl radical having 1 to 4 carbon atoms, and a pharmaceutically acceptable carrier.

7. A pharmaceutical composition as claimed in claim 6 which is useful in the treatment of rheumatoid arthritis.

8. A pharmaecutical composition as claimed in claim 6 which is useful in the immunotherapy of cancer.

9. A pharmaceutical composition as claimed in claim 6 which is useful in the treatment of viral diseases.

* * * * *